Figure 1:
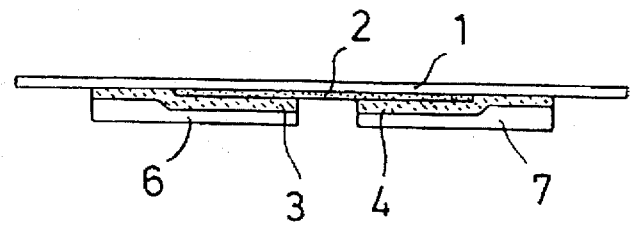

United States Patent [19]
Horstmann

[11] Patent Number: 5,685,837
[45] Date of Patent: Nov. 11, 1997

[54] GALVANICALLY ACTIVE TRANSDERMAL THERAPEUTIC SYSTEM

[75] Inventor: Michael Horstmann, Neuwied, Germany

[73] Assignee: LTS LohmannTherapie-Systeme GmbH & Co. KG, Neuwied, Germany

[21] Appl. No.: 696,672

[22] Filed: May 7, 1991

[30] Foreign Application Priority Data

May 10, 1990 [DE] Germany ............. 40 14 913.7

[51] Int. Cl.[6] ..................................... A61N 1/30
[52] U.S. Cl. ................. 604/20; 156/182; 427/2.12
[58] Field of Search ............... 604/20; 128/798, 128/802, 803, 639; 607/75, 115; 156/182, 306.3, 60; 427/2.12

[56] References Cited

U.S. PATENT DOCUMENTS

| | | | |
|---|---|---|---|
| 222,276 | 12/1879 | Hunter | 604/20 |
| 486,902 | 11/1892 | Shults | 604/20 |
| 542,459 | 7/1895 | Beckwith | 604/20 |
| 4,040,412 | 8/1977 | Sato | 128/640 |
| 4,211,222 | 7/1980 | Tapper | 604/20 |
| 4,474,570 | 10/1984 | Ariura et al. | 604/20 |
| 4,702,732 | 10/1987 | Powers et al. | 604/20 |
| 4,752,285 | 6/1988 | Petelenz et al. | 604/20 |
| 4,808,152 | 2/1989 | Sibalis | 604/20 |
| 4,950,229 | 8/1990 | Sage, Jr. | 604/20 |
| 5,084,006 | 1/1992 | Lew et al. | 604/20 |
| 5,087,242 | 2/1992 | Petelenz et al. | 604/20 |

FOREIGN PATENT DOCUMENTS 410009  5/1934  United Kingdom ............. 604/20

*Primary Examiner*—Mark Bockelman
*Assistant Examiner*—Ellen Tao
*Attorney, Agent, or Firm*—Sprung Kramer Schaefer & Briscoe

[57] ABSTRACT

A transdermal therapeutic system which is composed of layers exhibits an electrically insulating backing layer (1) being impermeable to active substances, and two galvanic elements which are positioned in separation from each other. The skin-facing electrodes of the galvanic elements have layers thereon consisting of a liquid absorbing material becoming ionically conductive after liquid admission. The layer of at least one of the dermad electrodes comprises a pharmaceutical active substance.

20 Claims, 1 Drawing Sheet

GALVANICALLY ACTIVE TRANSDERMAL THERAPEUTIC SYSTEM

DESCRIPTION

The present invention relates to a galvanically active transdermal therapeutic system.

The principle of the transcutaneous iontophoresis, i.e., the application of galvanic (electrostatic) electrical fields for the therapeutic introduction of ionic substances into human or animal tissues has been known for long (Pivati 1747, cited in Wearley, L. et al, J. Contr. Release 8, 237–250 (1989). Basically such systems are composed of at least one supply point and two electrodes which are insulated from each other, electrically conductive and lying on the human skin. In this connection, one of the electrodes contains a mostly ionic drug which is brought into the skin by the field strength of the electric field.

This principle has been applied, e.g., in experimental pharmacology to introduce ionic substances into animal tissues which initially are difficult to pass (for instance, microiontophoresis into certain parts of the brain). In clinical medicine, too, some fields of application have opened up, e.g., in the therapy of excessive secretion of sweat by means of tap-water-iontophoresis, or—in contrast thereto—in functional tests of the sweat glands by means of percutaneous iontophoretically administered pilocarpine. During the last decades, the importance of the iontophoresis has increasingly been realized for systemic percutaneous medication, in addition to the limited field of local treatment.

The so-called transdermal therapeutic systems are such forms of administration, which permit the controlled release of active substances to the whole organism through the skin.

Compared to the oral route this form of application is of great advantage, e.g., due to avoiding the first-pass-effect and prolonging the biological duration of effect. Unfortunately, the major portion of the active substances suitable for medicinal use do not sufficiently pass the skin—above all these are ionic drugs or those the molecular weight of which is too high. Since it is the cationic and anionic active substances which may pass through the skin by means of the iontophoresis, a therapeutically very interesting field has opened up.

In literature solutions are known which show a clear tendency to miniaturize. This starts with the fact that a battery which is incorporated into the apparatus is used instead of stationary current sources (U.S. Pat. No. 3,153, 166, DE 32 25 748, EP 0 240 593).

The selection or construction of suitable supply points for iontophoretic transdermal systems is decisive for the quality and the price of such devices—it is the use of small, light and inexpensive batteries consisting of physiologically acceptable materials. Conventional zinc-coal-dry batteries are too heavy and thus insuitable for this purpose. Mercury and lithium button-shaped cells, which were repeatedly proposed for the use in iontophoretic systems, are relatively light but too expensive. In addition, these elements partially comprise toxic substances (e.g., mercury); the capacity thereof is unnecessarily high so that used systems with nearly fresh batteries must either be disposed of or the source of energy (reusable) has to be separated from the electrodes (single use). However, in the latter case, one has to accept troublesome handling. In addition, the active substance supply may unpredictably be terminated due to the different service life of such batteries. Therefore, reliability is impaired.

The transport rate of the pharmacological active substance into the skin substantially depends on the intensity of current rather than on the electric potential within the iontophoretic field. Thus, according to Ohm's law, a varying skin resistance at a constant distribution voltage may cause a fluctuating iontophoretic current and thereby an unpredictable flow of active substances. For this reason, appliances for the stabilization of the electric current were proposed (e.g., EP 0 254 965).

Even if a constant strength of current is applied, interferences occur which change the active substance flow into the skin, in particular in case of a high current density. Therefore, due to the migration of hydrogen ions and hydroxyl ions, a pH-shift occurs which influences the proportion of ionic active substances and, as a consequence of differing migration velocities, the concentration ratios between active substance ions and accompanying ions from the environment (competitive ions) change.

Efforts were made to eliminate these problems, amongst others electronically controlled pulsation of the electric current was proposed (e.g., EP 0 060 451).

Additional apparatuses of this kind (stabilization of current, pulsation) can be realized today on a relatively small space, however, such systems thus become more complicated and expensive. For instance, EP 0 278 473 is directed to special spatial arrangements, EP 0 269 246, EP 0 252 732, EP 0 182 520 describe special electrodes on the skin side and mainly aim at a compacter design.

It is accordingly the object of the present invention to provide an iontophoretic transdermal therapeutic system which can be manufactured at a reasonable price, is comfortable and safe to handle, and is completely composed of physiologically acceptable substances.

According to the present invention this object is achieved by a transdermal therapeutic system having a laminated structure, a process for the production thereof, and the use thereof according to the features of the claims. The transdermal therapeutic system with layered structure comprises two sheet-like galvanic elements which are separately positioned and connected in series below an electrically insulating backing layer which is impermeable to active substances and an electrically conductive connecting layer, whereby the dermadly facing electrodes of these galvanic elements have layers thereon consisting of a liquid absorbing material which after liquid absorption is ionically conductive, whereby this layer of at least one of the dermad electrodes contains a pharmaceutically active substance e.g., an antirheumatic, antiasthmatic, antidiabetic, or antihypertensive. The features of the sub-claims contain additional advantageous embodiments of the transdermal therapeutic system according to the present invention.

In this connection, the current-time-characteristic of the battery itself is used to control the supply rate of the active substance. Thus, in case of a sufficiently high capacity of the supply point, it is possible, on the one hand, to create a constant intensity of current and thereby a constant active substance flow. On the other hand, the decreasing internal resistance of a low-capacity supply point may serve to create a gradually decreasing current intensity and thus lower transdermal active substance flow. In addition there is the possibility to render the transdermal therapeutic system activatable by moisture so that the electrical current, which starts to act with a delay in time, actuates and sustains the active substance flow with a predetermined delay in time. In contrast to EP 0 282 982, in which a "dry" transdermal iontophoretic system causes the displacement of the current flow to the larger stratum corneum by means of "shunts" which are filled with water, in the device according to the present invention an environment on the skin which becomes increasingly humid due to transepidermal loss of water may optionally serve to activate the sources of energy.

Figure 2:
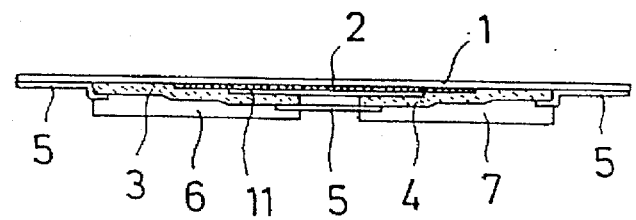
Figure 3:
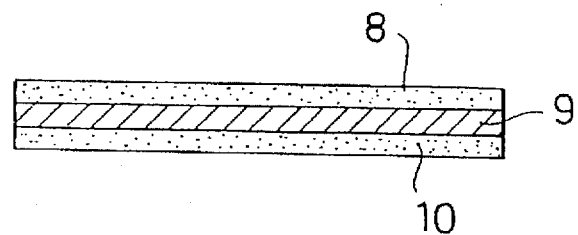
Figure 4:
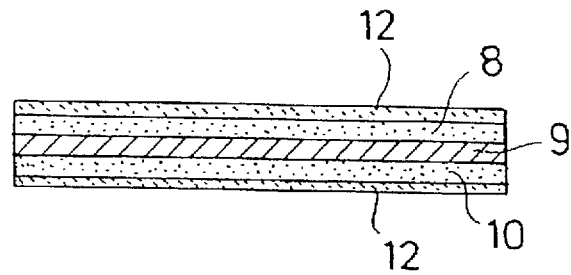

The invention will be further described with reference to the accompanying drawing wherein:

FIGS. 1 and 2 are vertical sections through different embodiments of transdermal systems in accordance with the present invention; and FIGS. 3 and 4 are vertical sections through different embodiments of galvanic cells which may be employed in the systems of FIGS. 1 and 2.

The construction of the galvanic cells (3, 4) according to the present invention basically corresponds to that of the Leclanche cell known and proven in dry batteries for decades. This cell is also known in numerous flat-shaped variations (e.g., JP 62 128 447). In principle, the negative electrode (8) of the element according to the present invention consists of a dispersion of zinc powder with a preferred particle size of 0.5 to 50 μm which is present in a polymer-containing layer connecting the particles. Suitable polymers are, for example, polyacrylic acid and the esters thereof, polyisobutylene, polyvinyl acetate copolymers, as well as materials having a similar function. Additives to adjust the hardness or tackifying additives may as well be suitable to improve the flexibility and the bond to the adjacent layers. Additives in the amount of preferably 1 to 20%-wt of coal or graphite are possible too; they may serve to improve the conductivity between the zinc particles. It is preferred that the portion of zinc is in the range of 60 to 95%-wt.

The positive electrode (10) consists of a common dispersion of manganese dioxide and coal or graphite, respectively, in a polymer or polymer-containing mass corresponding to that described for the negative electrode (8). The percentage by weight of the inorganic components may amount to about 40 to 95%-wt. In general, the amount of manganese dioxide is predominant over the graphite, however, this is not compelling.

The electrolytic layer (9) has to exhibit ionic conductivity and serve to prevent short circuits, i.e., it must exhibit mechanical strength. In order to meet these requirements the skilled artisan may choose out of a variety of possibilities.

To increase conductivity ionic substances may be added, for example, inorganic salts, particularly preferred are ammonium chloride or viscosity increasing substances, such as starch or polyvinyl alcohol. Suitable structural components are non-wovens, pacer of various qualities and thicknesses, porous plastic film and sheeting, or highly concentrated pastes of substantially inert substances (e.g., gypsum).

The thickness of the three individual layers of the elements is of no importance for the function; it may preferably range between 1 and 500 μm.

The production of the galvanic elements may be carried out layer by layer by either dissolution or suspension in a suitable solvent, spreading as a thin layer, and subsequent drying followed by-laminating the three layers on top of each other. It is also possible to spread, extrude or roll-out the positive and/or negative electrode in a hot melt process by using a thermoplastic polymeric mixture.

The electrolytic layer can also be produced by impregnating a paper, non-woven, or porous film with the solution of one or more electrolytes.

In case of insufficient conductivity between anode and cathode, the outer surfaces of the elements may be coated with an additional conductive layer (12) the inorganic component of which is carbon. The same polymeric mixtures as described for the cathode and anode of the elements can be used as binders.

The skin-facing electrodes with the conductive layers (6, 7) of the transdermal therapeutic system are located in a flush or slightly overlapping manner directly on the cathode or anode of the galvanic elements which are connected in series.

They consist of a non-woven, paper, gel, or a foil being porous, impermeable to water vapor and water-absorbing and which may be provided with active substances, electrolytes, and, optionally, additional substances. Cationic active substances are preferably placed under the positive pole, anionic ones below the negative pole.

On the side averted from the skin, the two galvanic cells are conductively connected with each other via an electrically conductive connecting layer (2) of, e.g., aluminum, aluminized foil, or a material corresponding to those described above in connection with optional additional conductive layers.

To exclude short circuits or local element formation between the dermad electrodes and the electrical potential of the connecting layer, an insulating layer (5), and optionally a further layer (11) according to FIG. 2, may be applied as mask. This may consist of any desired physiologically acceptable material having a sufficient electrically insulating effect, e.g., polyisobutylene, polyurethane polyethylene, polyethylene terephthalate, silicone rubber, or polyvinyl acetate and the copolymers thereof.

To fix the therapeutic system to the skin, insulating layer and backing layer may be pressure-sensitive adhesive. This may be effected, for example, by previous application of a substantially nonconducting layer of polyacrylates, rubber-resin-mixtures, and substances having the same functions.

Prior to use the system may be covered on the side facing the skin with a dehesive protective film for the purpose of protection. If desired, water used in the production of the device according to the present invention may almost completely be removed by drying in order to improve the storing properties thereof. In this connection, the device is preferably stored in a suitable package being impermeable to water vapor (e.g., an aluminized sealed big of composite material).

Prior to use this embodiment of the subject matter of the present invention is activated by short-time insertion into a water-saturated atmosphere, or by dipping it into water. Due to diffusion moisture also reaches the electrolytic layers of the galvanic cells through the polymers. A particularly mild way of activation is effected when water vapor from the skin penetrates into the system after it has been placed on the skin in still dry condition (occlusive effect/perspiratio insensibilis).

An important advantage of the system is the fact that the intensity of current and thus the active substance flow is determined in a reproducible way by the system-inherent internal resistance and that it may be adapted to the therapeutic requirements by a corresponding design of the cells. If, for instance, a smoothly decreasing release rate is desired already during wearing the system, the electrodes of the galvanic elements are designed in a very thin way so that the iontophoretic current decreases in a predetermined and reproducible manner due to gradual consumption of active electrode material. This would be useful, amongst others, in therapies which have to be adjusted to a specific time of day.

As a whole the structure according to the present invention considerably facilitates handling since electrical control units and the like are unnecessary. The appliance can therefore be produced at a reasonable price and is more comfortable to wear than the systems according to the state of the art.

FIGS. 1 to 4 show the entire structure of the system according to the present invention:

FIG. 1:
1—backing layer, impermeable to active substances
2—electrically conductive connecting layer
3,4—sheet-like galvanic elements
6,7—ionically conductive layers, optionally containing active substances FIG. 2:
1—backing layer, impermeable to active-substances
2—electrically conductive connecting layer
3,4—sheet-like galvanic elements
5—insulating layer provided with recesses
6,7—ionically conductive layers, optionally containing active substances
11—additional insulating layer FIG. 3:
8—pulverized zinc containing layer
9—electrolytic layer
10—manganese dioxide and carbon containing layer FIG. 4:
8—pulverized zinc containing layer
9—electrolytic layer
10—manganese dioxide and carbon containing layer
12—conductive layer, containing pulverized carbon The invention is illustrated by means of the following examples:

EXAMPLE 1

Production of a sheet-like galvanic element:
Phase 1:
  100 g zinc, finely powdered
  15 g graphite, finely powdered
  10 g copolymer of vinyl acetate and vinyl laurate [Vinnapas B500/40VL (Wacker)]
are dissolved or suspended in 20 g 2-butanone
Phase 2:
  80 g manganese dioxide, finely powdered
  25 g graphite, finely powdered
  10 g copolymer of vinyl acetate and vinyl laurate [Vinnapas B500/40VL (Wacker)]
are also suspended in 60 g 2-butanone.

Fine writing paper (60 g/m$^2$) is impregnated with a solution of
  3.8 g ammonium chloride and
  1.0 g polyvinylpyrrolidone in 20 ml water
so that after drying a mass per unit area of approximately 90 g/m$^2$ results.

The paper is coated with a layer of phase 1 at a thickness of 200 μm. After drying, the same paper is coated on the other side with a layer of phase 2 at a thickness of 300 μm.

The element is dried at 100° C. for 10 minutes and subsequently stored protected from moisture.

EXAMPLE 2

Production of a galvanically active transdermal therapeutic system (cf. FIG. 2)

A piece of 25×25 mm aluminum foil (2) (thickness approx. 10 μm) is centrally placed on a 50×50 mm piece of polyester foil (25 μm) which serves as backing layer (1) and was rendered adhesive by applying 40 g/m$^2$ Durotak 280-2516 [a tacky acrylate-copolymer of National Starch & Chemical].

An adhesive strip (11) of 6×50 mm size made of the same material as (1) is placed on the aluminum layer in such a way that the square is divided into two commensurate rectangles.

Two pieces of 27×30 mm each are cut from the sheetlike material produced according to Example 1. These pieces (3 and 4) are positioned according to FIG. 2 in such a way that the two conductive aluminum surfaces are covered with overlap and that the two elements do not contact each other. In this connection, the zinc layer is on the top of one element, and the manganese dioxide layer on top of the other one. In accordance with the drawing the energy supplying portion is covered with a mask (5) of a tacky soft film of Durotak 280-2516 at a thickness of 60 μm. Finally, the two 27×30 mm non-woven supports (6 and 7) are anchored on this layer. Prior to that 0.1 ml 1% epinephrine-hydrochloride-solution was dripped on the non-woven carrier to be positioned on the zinc surface; it was then mildly dried at room temperature. The counter-lateral non-woven is correspondingly dripped with 0.1 ml 1% sodium hydrogen-phosphate solution and dried.

It is understood that the specification and examples are illustrative but not limitative of the present invention and that other embodiments within the spirit and scope of the invention will suggest themselves to those skilled in the art.

What is claimed is:

1. A therapeutic system for carrying out transdermal iontophoretic therapies with a flexible, laminated layered structure, comprising a backing layer (1) which is impermeable to active substances as well as two sheet-like galvanic elements (3,4) having skin-facing electrodes, positioned separately from each other and connected in series via an electrically conductive connecting layer (2), which galvanic elements are positioned in reversed arrangement of anode and cathode the same distance from a surface of the backing layer (1), the skin-facing electrodes of said galvanic elements having ionically conductive layers (6,7) thereon made of a material which absorbs moisture and, after absorption of moisture becomes ionically conductive, an ionically conductive layer (6,7) on at least one of the skin-facing electrodes containing a pharmaceutically active substance, any chemicals in any layer, being in thermally dried condition.

2. A transdermal therapeutic system according to claim 1, wherein the system is enclosed in a package which is impermeable to water vapor.

3. A transdermal therapeutic system according to claim 1, wherein the galvanic elements (3,4) comprise a layer structure of a pulverized zinc-containing layer (8), an electrolytic layer (9), and a further layer of pulverized manganese dioxide carbon, the thickness of the individual layers ranging from 1 to 500 μm.

4. A transdermal therapeutic system according to claim 1, wherein the basic material of any electrodes and any electrically conductive layers comprises at least one of polymers and copolymers of vinyl acetate or acrylic acid and esters thereof, polyurethane and polyisobutylene.

5. A transdermal therapeutic system according to claim 1, wherein said pharmaceutically active substance is a cationic active substance or an anionic active substance and wherein said cationic active substance is present under the anode and said anionic active substance is present under the cathode.

6. A transdermal therapeutic system according to claim 1, wherein the active substance is an antirheumatic, antiasthmatic, antidiabetic or antihypertensive.

7. A transdermal therapeutic system according to claim 1, including an insulating layer (5) to avoid short circuits or local element formulation, said insulating layer (5) being partially positioned between galvanic elements (3,4) and conductive layers (6,7) and further including recesses positioned between galvanic elements (3,4) and conductive layers (6,7).

8. A transdermal therapeutic system according to claim 7, wherein the insulating layer (5) is provided with a pressure-sensitive adhesive finish to fix the system to the skin.

9. A transdermal therapeutic system according to claim 1, including an insulating layer (11) positioned between the galvanic elements (3,4) and the connecting layer (2) to avoid short circuits or local element formation.

10. A transdermal therapeutic system according to claim 1, wherein active substance flow from an ionically conductive layer containing said active substance is subject to control by electrical internal resistance.

11. A transdermal therapeutic system according to claim 1, wherein the capacity of the galvanic element is adjusted so that a constant active substance flow is achieved by means of a constant strength of current.

12. A transdermal therapeutic system according to claim 1, wherein the outer surface of at least one of the electrodes (8,10) carries an additional conductive layer (12) containing pulverized carbon.

13. A transdermal therapeutic system according to claim 1, which comprises forming the galvanic elements layer by layer by either dissolution or suspension in a solvent, spreading each as a thin layer, drying, and subsequently laminating the three layers on top of each other.

14. A process for the production of a transdermal therapeutic system according to claim 1, wherein the electrodes are spread, extruded, or rolled-out in a hot-melt-process using a thermoplastic polymeric mixture.

15. A transdermal therapeutic system according to claim 1, wherein an electrolytic layer on the galvanic elements is obtained by impregnating a paper, non-woven, or porous foil with the solution of an electrolyte.

16. In the use of the transdermal therapeutic system according to claim 1, the improvement which comprises first activating the system by short-time insertion into a water saturated atmosphere, or by dipping into water.

17. In the use of the transdermal therapeutic system according to claim 1, the improvement which comprises placing the system on the skin in dry condition, whereupon the system is activated by means of water vapor from the skin penetrating into the system.

18. A therapeutic system for carrying out transdermal iontophoretic therapies with a flexible, laminated layered structure, comprising a package impermeable to water vapor and containing a laminated structure comprising a backing layer (1) which is impermeable to active substances as well as two sheet-like galvanic elements (3,4) having skin-facing electrodes, positioned separately from each other and connected in series via an electrically conductive connecting layer (2), which galvanic elements are positioned in reversed arrangement of anode and cathode the same distance from a surface of the backing layer (1), the galvanic elements (3,4) comprising a multi-layer structure, the thickness of the individual layers ranging from 1 to 500 µm, the skin-facing electrodes of said galvanic elements having ionically conductive layers (6,7) thereon made of a material which absorbs moisture and, after absorption of moisture becomes ionically conductive, the basic material of the electrodes and any electrically conductive layers comprising at least one of polymers and copolymers of vinyl acetate or acrylic acid and esters thereof, polyurethane and polyisobutylene, an ionically conductive layer on at least one of the skin-facing electrodes containing a pharmaceutically active substance, any chemicals in any layer being in thermally dried condition.

19. A transdermal therapeutic system according to claim 18, including an insulating layer (5) to avoid short circuits or local element formulation, said insulating layer (5) being partially positioned between galvanic elements (3,4) and conductive layers (6,7) and further including recesses positioned between galvanic elements (3,4) and conductive layers (6,7).

20. A process for producing a packaged transdermal therapeutic system for transdermal iontophoretic therapies with a therapeutic system for carrying out transdermal iontophoretic therapies with a flexible, laminated structure, comprising a package impermeable to water vapor and containing a laminated structure comprising a backing layer (1) which is impermeable to active substances as well as two sheet-like galvanic elements (3,4) having skin-facing electrodes, positioned separately from each other and connected in series via an electrically conductive connecting layer (2), which galvanic elements are positioned in reversed arrangement of anode and cathode the same distance from a surface of the backing layer (1), the galvanic elements (3,4) comprising a multi-layer structure, the thickness of the individual layers ranging from 1 to 500 µm, the skin-facing electrodes of said galvanic elements having ionically conductive layers (6,7) thereon made of a material which absorbs moisture and, after absorption of moisture becomes ionically conductive, the basic material of the electrodes and any electrically conductive layers comprising at least one of polymers and copolymers of vinyl acetate or acrylic acid and esters thereof, polyurethane and polyisobutylene, an ionically conductive layer on at least one of the skin-facing electrodes containing a pharmaceutically active substance, any chemicals in any layer, being in thermally dried condition, wherein said process comprises forming the galvanic elements layer by layer by either dissolution or suspension in a solvent, spreading each as a thin layer, drying, and subsequently laminating the three layers on top of each other, the electrodes being spread, extruded, or rolled-out in a hot-melt-process using a thermoplastic polymeric mixture, an electrolytic layer on the galvanic elements being obtained by impregnating a paper, non-woven, or porous foil with the solution of an electrolyte, drying the laminated layered structure thereby almost completely removing any water, and sealing the laminated layered structure in a water vapor-impermeable package.

* * * * *